United States Patent
Crumblin et al.

(10) Patent No.: US 9,878,117 B2
(45) Date of Patent: Jan. 30, 2018

(54) SWIVEL ELBOW FOR MASK ASSEMBLY

(75) Inventors: Geoffrey Crumblin, Baulkham Hills (AU); Craig David Edwards, Annandale (AU); Daniel Robert Judson, Lapstone (AU); Bryony Louise Marshall, Westleigh (AU)

(73) Assignee: RESMED LIMITED, Bella Vista (AU)

( * ) Notice: Subject to any disclaimer, the term of this patent is extended or adjusted under 35 U.S.C. 154(b) by 3245 days.

(21) Appl. No.: 11/922,140

(22) PCT Filed: Jun. 5, 2006

(86) PCT No.: PCT/AU2006/000768
§ 371 (c)(1),
(2), (4) Date: Dec. 13, 2007

(87) PCT Pub. No.: WO2006/133480
PCT Pub. Date: Dec. 21, 2006

(65) Prior Publication Data
US 2010/0083969 A1    Apr. 8, 2010

Related U.S. Application Data

(60) Provisional application No. 60/690,870, filed on Jun. 16, 2005.

(51) Int. Cl.
*A61M 16/06* (2006.01)
*A61M 16/08* (2006.01)

(52) U.S. Cl.
CPC ............ *A61M 16/06* (2013.01); *A61M 16/08* (2013.01); *A61M 16/0825* (2014.02); *A61M 16/0683* (2013.01); *A61M 16/0816* (2013.01); *A61M 2205/42* (2013.01)

(58) Field of Classification Search
CPC ... A61M 16/06; A61M 16/08; A61M 16/0825
USPC ............ 128/200.24, 201.13, 202.27, 203.12, 128/203.15–203.17, 203.26, 203.27, 128/204.17, 204.18, 204.21, 206.21, 912; 285/274, 276
See application file for complete search history.

(56) References Cited

U.S. PATENT DOCUMENTS

| | | | | |
|---|---|---|---|---|
| 3,461,877 A | * | 8/1969 | Ernst | 128/207.14 |
| 3,941,567 A | * | 3/1976 | Combaz | 422/80 |
| 4,252,332 A | * | 2/1981 | Nakayama et al. | 277/641 |
| 4,626,003 A | * | 12/1986 | Williams et al. | 285/98 |
| 4,736,969 A | * | 4/1988 | Fouts | 285/247 |

(Continued)

FOREIGN PATENT DOCUMENTS

| | | |
|---|---|---|
| DE | 197 57 703 | 10/1999 |
| DE | 202 01 347 | 5/2002 |
| GB | 2 069 849 | 9/1981 |

OTHER PUBLICATIONS

International Search Report for PCT/AU2006/000768 dated Aug. 30, 2006.

(Continued)

*Primary Examiner* — LaToya M Louis
(74) *Attorney, Agent, or Firm* — Nixon & Vanderhye, P.C.

(57) ABSTRACT

A swivel elbow for a mask assembly includes an elbow adapted to be provided to the mask assembly and a swivel detachably connected to the elbow. The elbow includes a plurality of spaced apart rings that provide a controlled clearance between the elbow and an interior surface of the swivel.

19 Claims, 21 Drawing Sheets

(56) References Cited

U.S. PATENT DOCUMENTS

| | | | |
|---|---|---|---|
| 4,783,100 A * | 11/1988 | Klein | 285/276 |
| D313,277 S | 12/1990 | Haining | |
| 5,062,420 A | 11/1991 | Levine | |
| 5,110,161 A * | 5/1992 | Bartholomew | 285/281 |
| 5,123,677 A | 6/1992 | Kreczko et al. | |
| 5,568,946 A | 10/1996 | Jackowski | |
| 5,964,485 A | 10/1999 | Hame et al. | |
| 6,192,886 B1 | 2/2001 | Rudolph | |
| 6,257,626 B1 | 7/2001 | Campau | |
| 6,279,573 B1 | 8/2001 | Johnson et al. | |
| 6,615,830 B1 | 9/2003 | Serowski et al. | |
| 2003/0094177 A1* | 5/2003 | Smith et al. | 128/204.18 |
| 2004/0166789 A1* | 8/2004 | Ashjaee et al. | 451/388 |
| 2004/0168690 A1* | 9/2004 | Payne | 128/207.14 |
| 2005/0172969 A1* | 8/2005 | Ging et al. | 128/206.24 |
| 2008/0215148 A1* | 9/2008 | Lesinski et al. | 623/10 |

OTHER PUBLICATIONS

Written Opinion of the International Searching Authority Aug. 30, 2006.
U.S. Appl. No. 11/027,689, filed Jan. 3, 2005 (p. 1 of specification, U.S. Publication No. 2005/0172969).
International Preliminary Report on Patentability for PCT/AU2006/000768, dated Dec. 17, 2007, 5 pgs.

* cited by examiner

SWIVEL ELBOW FOR MASK ASSEMBLY

CROSS-REFERENCE TO RELATED APPLICATIONS

This application is the U.S. national phase of International Application No. PCT/AU2006/000768, filed 5 Jun. 2006, which designated the U.S. and claims the benefit of U.S. Provisional Application No. 60/690,870, filed Jun. 16, 2005, each of which is incorporated herein by reference in its entirety.

FIELD OF THE INVENTION

The present invention relates to a swivel elbow for use with a mask assembly for Non-invasive Positive Pressure Ventilation (NIPPY) and for continuous positive airway pressure (CPAP) therapy of sleep disordered breathing (SDB) conditions such as obstructive sleep apnea (OSA).

BACKGROUND OF THE INVENTION

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A washout vent in the mask or conduit discharges the exhaled gas from the mask atmosphere.

Known masks include a swivel elbow provided to the frame. The swivel elbow receives pressurized breathable gas from a suitable source of pressurized air. The leak rate through the swivel elbow forms part of the overall leak rate from the mask, incorporating the vent flow rate and the mask leak at the cushion of the mask. One key purpose of the vent flow rate is to provide sufficient $CO_2$ washout from the mask. It is advisable to control the flow rate from the mask in order to provide constant known characteristics to the flow generator for prediction of pressure, flow and leakage from the cushion of the mask. Excessive leakage from the swivel elbow may also lead to noise and disturbance to the patient.

SUMMARY OF THE INVENTION

One aspect of the invention relates to a swivel elbow that reduces the leak rate at the elbow/swivel interface and reduces the variation in the leak rate at this interface.

Another aspect of the invention relates to a swivel elbow that allows ease of swivel.

Another aspect of the invention relates to a swivel elbow for a mask assembly including an elbow adapted to be provided to the mask assembly and a swivel detachably connected. to the elbow. The elbow includes a plurality of spaced apart rings that provide a controlled clearance between the elbow and an interior surface of the swivel.

Another aspect of the invention relates to a swivel elbow for a mask assembly including an elbow adapted to be provided to the mask assembly and a swivel detachably connected to the elbow. The elbow includes a lip seal that provides a controlled interference between the elbow and the swivel.

Another aspect of the invention relate's to a swivel elbow for a mask assembly including an elbow adapted to be provided to the mask assembly and a swivel detchably connected to the elbow. The elbow forms a seal with the swivel at two sealing locations.

Another aspect of the invention relates to a swivel elbow for a mask assembly including an elbow adapted to be provided to the mask assembly and a swivel detachably connected to the elbow. The swivel includes a lip seal that provides a controlled interference between the elbow and the swivel.

Yet another aspect of the invention relates to a swivel elbow for a mask assembly including an elbow adapted to be provided to the mask assembly and a swivel detachably connected to the elbow. The elbow includes a saw-toothed or waved shaped exterior surface that is structured to engage hi complementary relation a saw-toothed or waved shaped interior surface of the swivel.

Still another aspect of the invention relates to a swivel elbow for a mask assembly including an elbow adapted to be provided to the mask assembly and a swivel detachably connected to the elbow. The swivel includes a flexible spring arm that provides a controlled interference between the elbow and the swivel.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 7b is a cross-sectional view of the swivel elbow shown in FIG. 7a;

DETAILED DESCRIPTION OF ILLUSTRATED EMBODIMENTS

1. Related Art Mask Assembly

Figure 1:
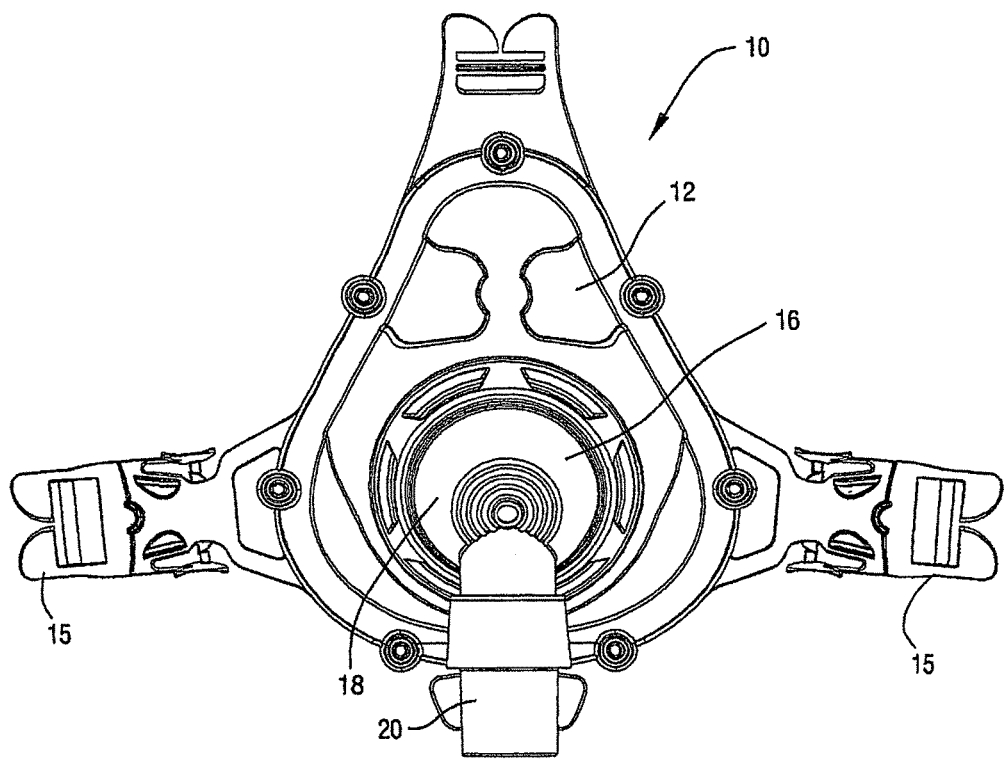
FIG. 1 is a front view of a respiratory mask assembly including a swivel elbow.
Figure 2:
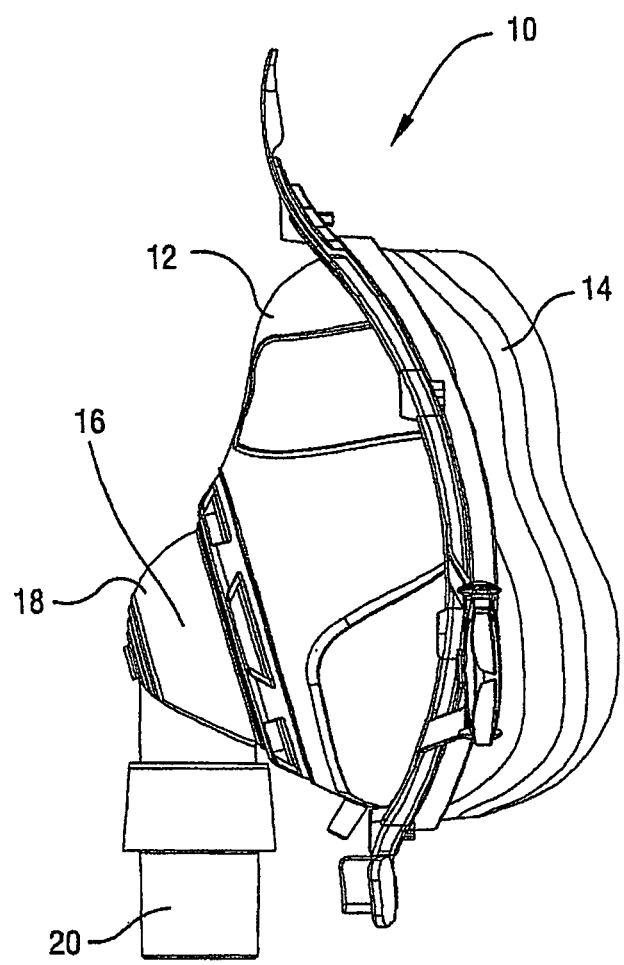
FIG. 2 is aside view of the respiratory mask assembly shown in FIG. 1.

FIGS. 1-2 illustrate a mask assembly 10 disclosed in U.S. patent application Ser. No. 11/027,689, filed Jan. 3, 2005, the entirety incorporated herein by reference. As illustrated, the mask assembly 10 includes a frame 12 in the form of a shell, and a cushion 14 that is provided, e.g., attached, to the frame 12. A headgear assembly (not shown) may be removably attached to the frame 14, e.g., via headgear clips 15, to maintain the frame 14 and cushion 14 in a desired adjusted position on the patient's face. A swivel elbow 16 is rotatably coupled or provided to the frame 12. The swivel elbow 16 is structured to be connected to an air delivery tube that delivers breathable gas to the patient.

2. Related Art Swivel Elbow

Figure 3:
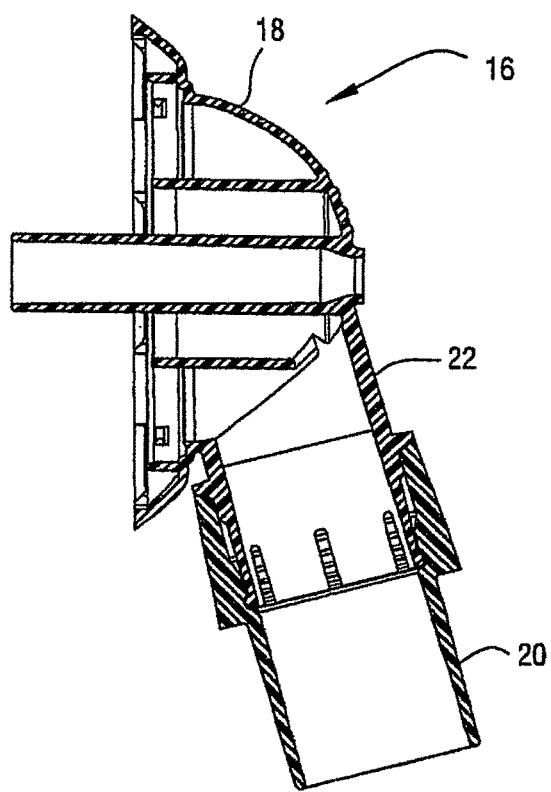
FIG. 3 is a cross-sectional view of the swivel elbow shown in FIG. 1 removed from the respiratory mask assembly.
Figure 4:
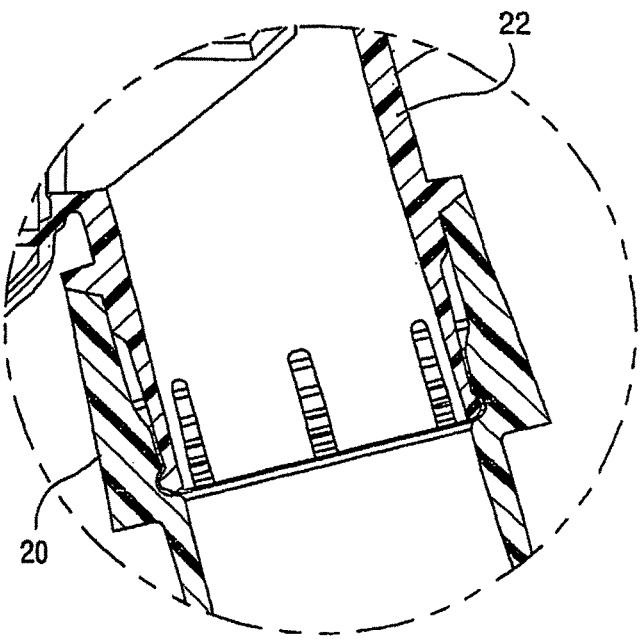
FIG. 4 is an enlarged cross-sectional view of the swivel elbow shown in FIG. 3.
Figure 5:
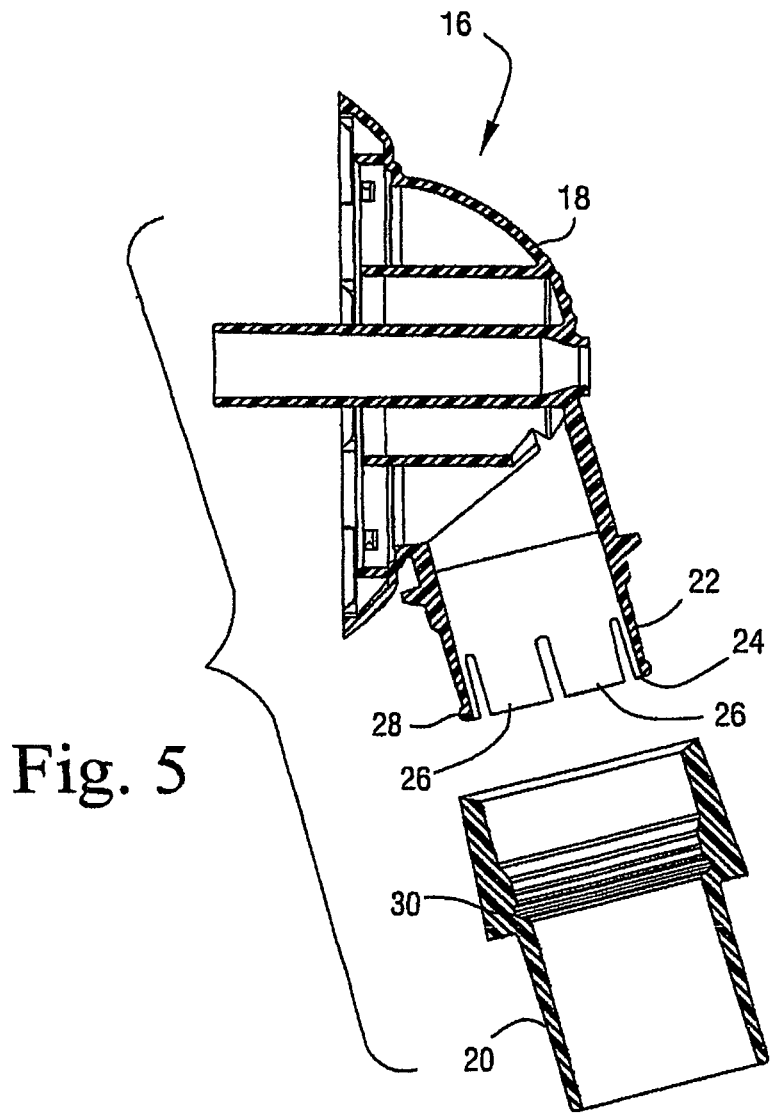
FIG. 5 is an exploded cross-sectional view of the swivel elbow shown in FIG. 1 removed from the respiratory mask assembly.

FIGS. 3-5 show the swivel elbow 16 of the mask assembly 10 in greater detail. The swivel elbow 16 includes an elbow 18 and a swivel 20 rotatably coupled to the elbow 18. As best shown in FIGS. 5, the elbow 18 includes an inlet conduit 22 having a hose end 24 with a plurality of resiliently deformable tabs 26 that are structured to allow selective attachment to and detachment from the swivel 20 with a snap-fit. Each tab 26 includes a radially extending protrusion 28 that locks in place within an interior groove 30 of the swivel 20. FIGS. 3 and 4 show the assembled position. The elbow 18 is preferably made from a polyester, e.g., natural POCAN®, a Bayer product, although other materials are possible. The swivel 20 may be made of clear polycarbonate, although other materials are possible. Further details of the swivel elbow 16 are provided in the above-noted U.S. patent application Ser. No. 11/027,689.

3. Swivel Elbows with Leak Restricting Features

FIGS. 1-5 illustrate one embodiment of a swivel elbow 16 having a snap-fit elbow/swivel connection. FIGS. 6-39 illustrate additional embodiments of swivel elbows that provide leak restricting features to improve the seal between the elbow and the swivel and to obtain a desired or controlled leak rate. While aspects of the invention are described with reference to a swivel elbow of the type described above, it is also applicable to other swivel elbows or other swivel conduits. That is, the swivel elbow is merely exemplary, and the sealing relationship between the swivel and the elbow may be incorporated into other swivel elbows or other swivel conduits of any suitable mask assembly, e.g., full-face mask, mouth mask, or a nasal mask.

As described in greater detail below, the leak restricting feature (e.g., leak restrictor) is provided at the swivel/elbow interface and may be in the form of a controlled clearance, a controlled interference, and/or a longer sealing path. It is noted that FIGS. 9-39 show portions of a swivel elbow, e.g.; a swivel and an end portion of an elbow. It should be understood that the remaining portion of the swivel may be similar to the swivel elbow of the type describe above or any other suitable swivel elbow or swivel conduit.

3.1 Controlled Clearance Between Swivel/Elbow

To control the leak rate between the swivel and the elbow, the swivel interface of the elbow may be provided with a controlled clearance that does not significantly effect the ease of rotation.

3.1.1 Separate Rings in the Sealing Diameter

In order to provide an enhanced sealing capacity between the elbow and the existing swivel, the elbow may incorporate at least one sealing ring of approximately the same wall thickness as the rest of the elbow. This arrangement improves the moldability of the part, and therefore improves the roundness and enhances the sealing capacity with the existing swivel 20.

Figure 6:
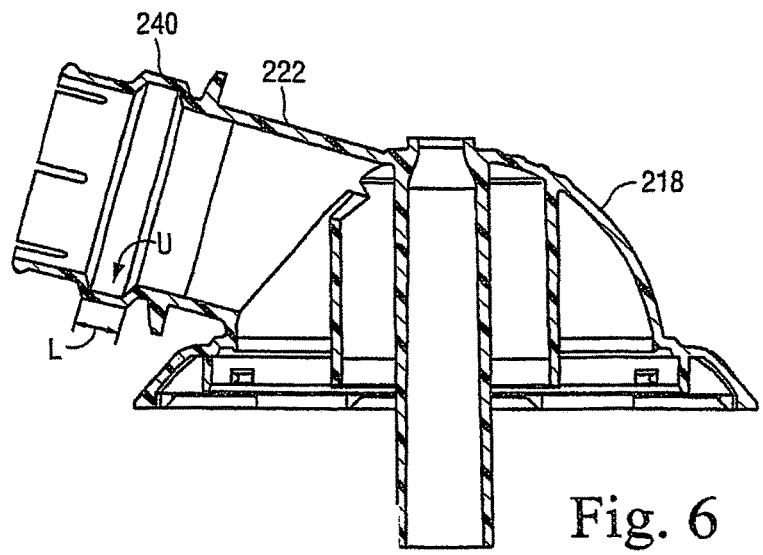
FIG. 6 is a cross-sectional view of a swivel elbow constructed according to an embodiment of the present invention.

One embodiment of this aspect of the invention is shown in FIG. 6. As illustrated, the inlet conduit 222 of the elbow 218 includes a sealing ring 240 that provides a controlled small clearance of about 0.05-0.3 mm between the elbow 218 and the swivel 20. Undercut U allows the sealing ring 240 to maintain a thickness similar to the rest of the elbow 218 and this in turn allows the length L of the sealing ring 240 to be greater than the thickness of the elbow 218. The increased length of the sealing ring 240 increases the length of small clearance and hence reduces leakage flow.

Figure 7A:
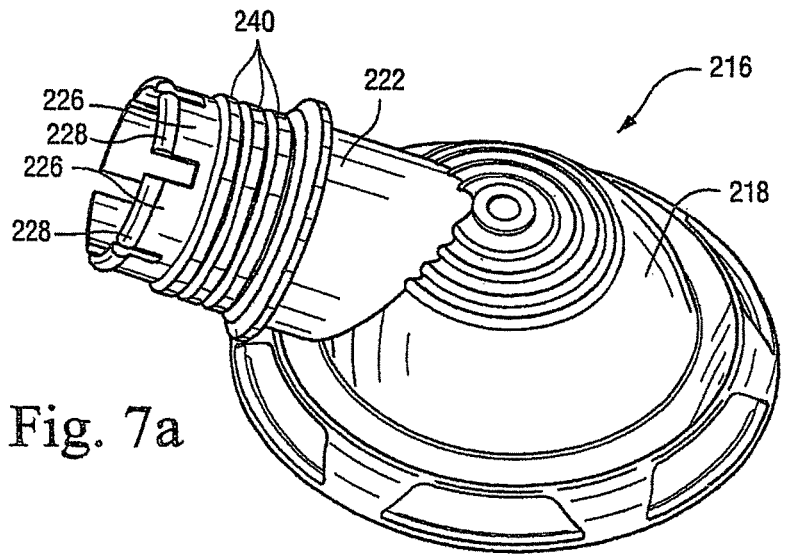
FIG. 7a is a perspective view of a swivel elbow constructed according to another embodiment of the present invention.
Figure 7B:
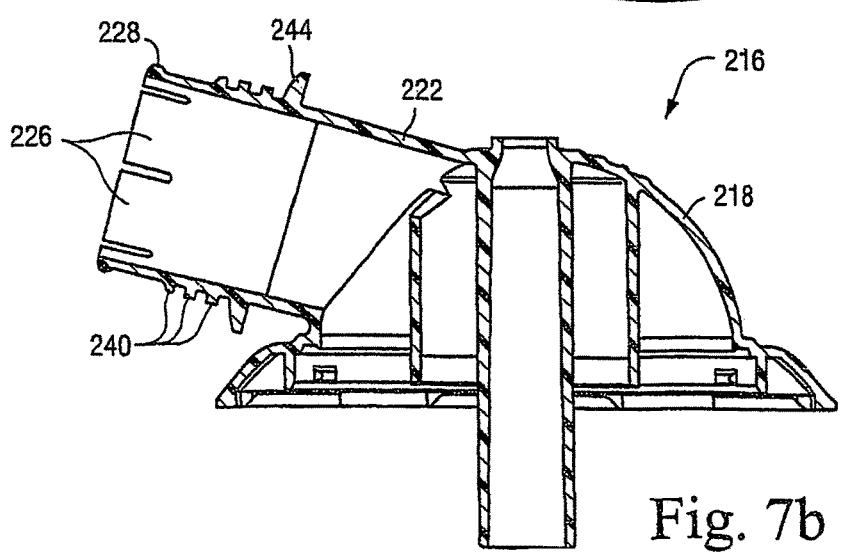
Figure 8:
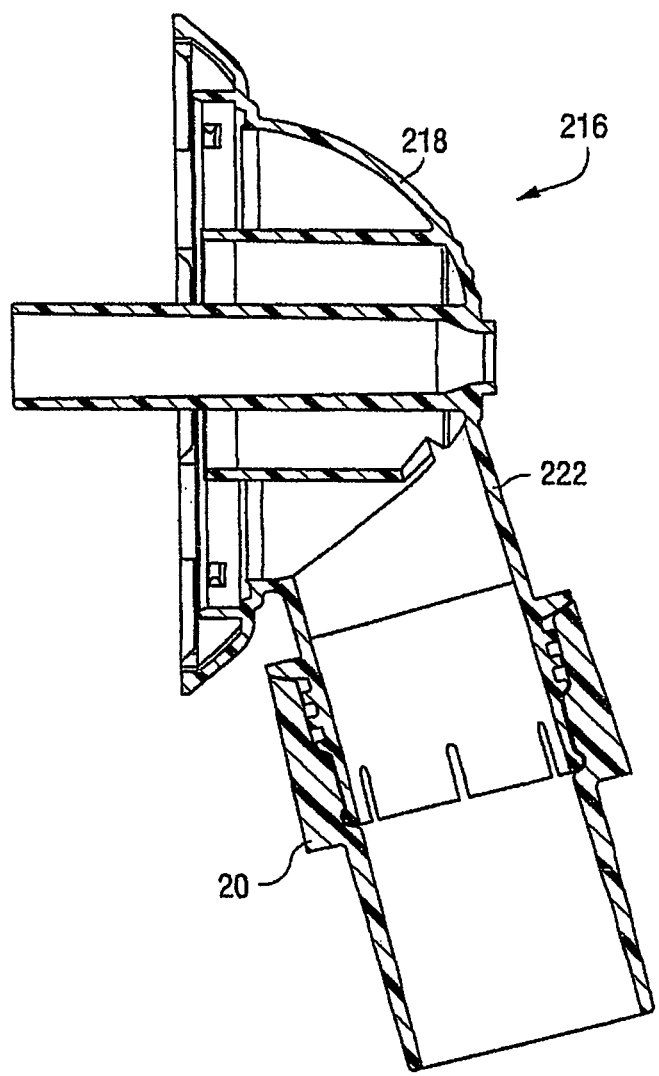
FIG. 8 is a cross-sectional view of the swivel elbow shown in FIG. 7a including a swivel.

FIGS. 7a, 7b, and 8 illustrate a swivel elbow 216 constructed according to another exemplary embodiment of the present invention. As illustrated, the inlet conduit 222 of the elbow 218 includes three separate rings 240 in the sealing interface or sealing diameter region. This arrangement provides a controlled clearance of about 0.05-0.3 mm between the elbow 218 diameter and the swivel 20 diameter. The controlled clearance helps to reduce the leak rate and control the variation in the leak rate between these two parts.

Specifically, the sealing diameter region of the elbow 218 is split into three separate rings 240 each having a width of about 1 mm and spaced apart from one another by about 1.2 mm. This arrangement maintains uniform wall sections throughout the elbow 218 to improve the moldability and therefore control clearance. The remaining portions of the inlet conduit 222 remain substantially similar to the inlet conduit 22, e.g., resiliently deformable tabs 226 with protrusions 228 to allow selective attachment to and detachment from the swivel 20 with a snap-fit. FIG. 8 shows the assembled position. It is noted that any suitable number of rings 240 may be provided, e.g., less than or greater than three rings.

In the illustrated embodiment, the swivel elbow 216 controls leak without significantly increasing the rotational resistance. Additionally, the width of the collar 244 at the outer rim may be reduced, or the draft angle on the back face of the collar 244 may be reduced in order to reduce the wall section in this area of the elbow 218 to improve the moldability of the part. Indeed, a further embodiment may have no collar 244.

3.2. Controlled Interference or Interface Between Swivel/Elbow With Lip Seal

Instead of controlling the clearance between the elbow and the swivel as described above in FIGS. 6-8, a controlled interference or interface in the form of an insert Molded (co-molded) lip seal may be provided to maintain the rotational resistance between the elbow and the swivel at required limits. This controlled interface provides a constricted flow path to improve seal. In the illustrated embodiments, the lip seal is formed of a TPE material (thermoplastic elastomer) or a similar suitable material.

3.2.1 Insert Molded TPE (Internal Lip)

Figure 9:
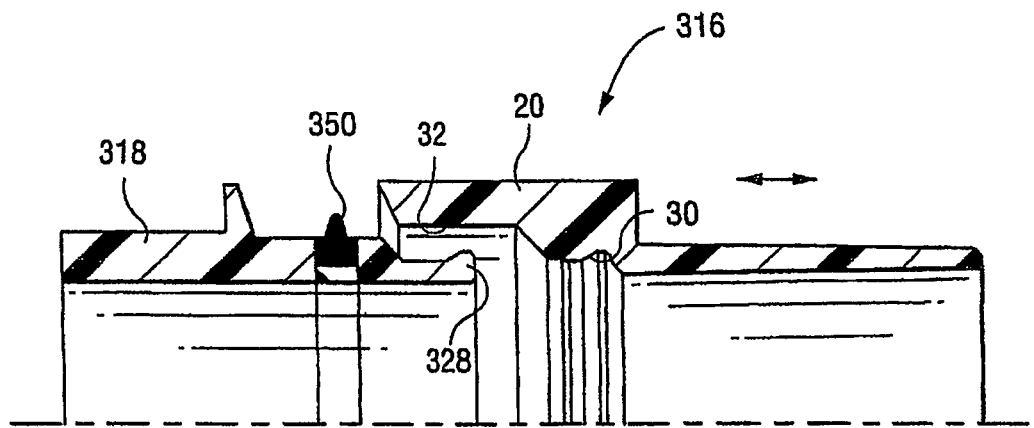
FIGS. 9-10 are cross-sectional views of a portion of a swivel elbow constructed according to another embodiment of the present invention in partial and fully connected states.
Figure 10:
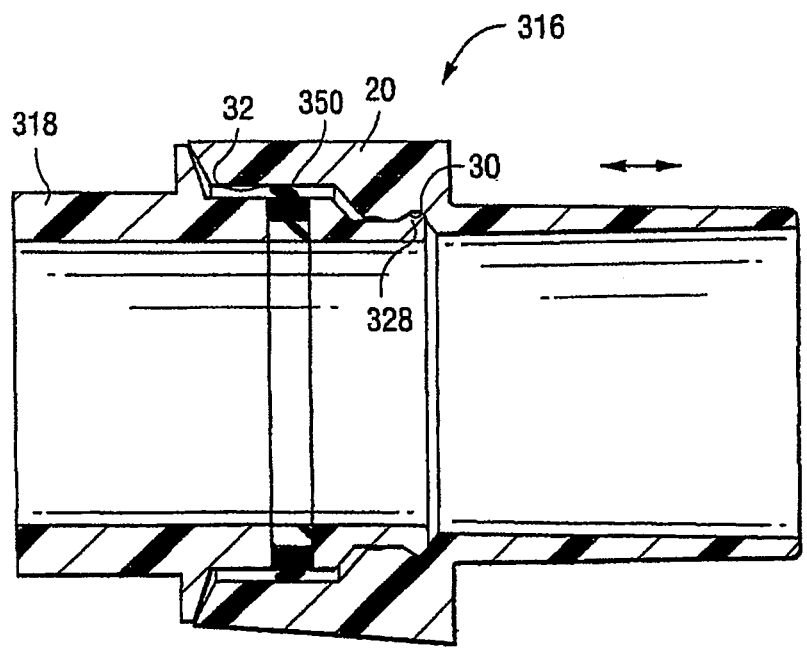
Figure 11:
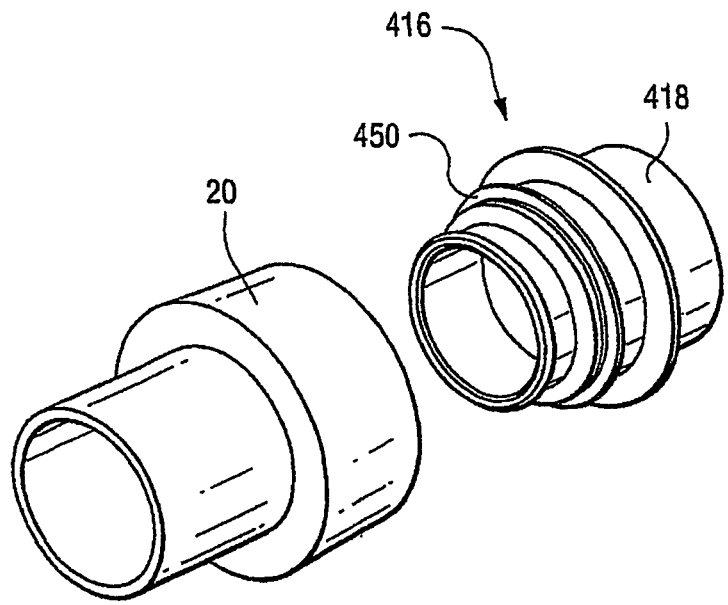
FIGS. 11-12 are perspective views of a portion of a swivel elbow constructed according to another embodiment of the present invention.
Figure 12:
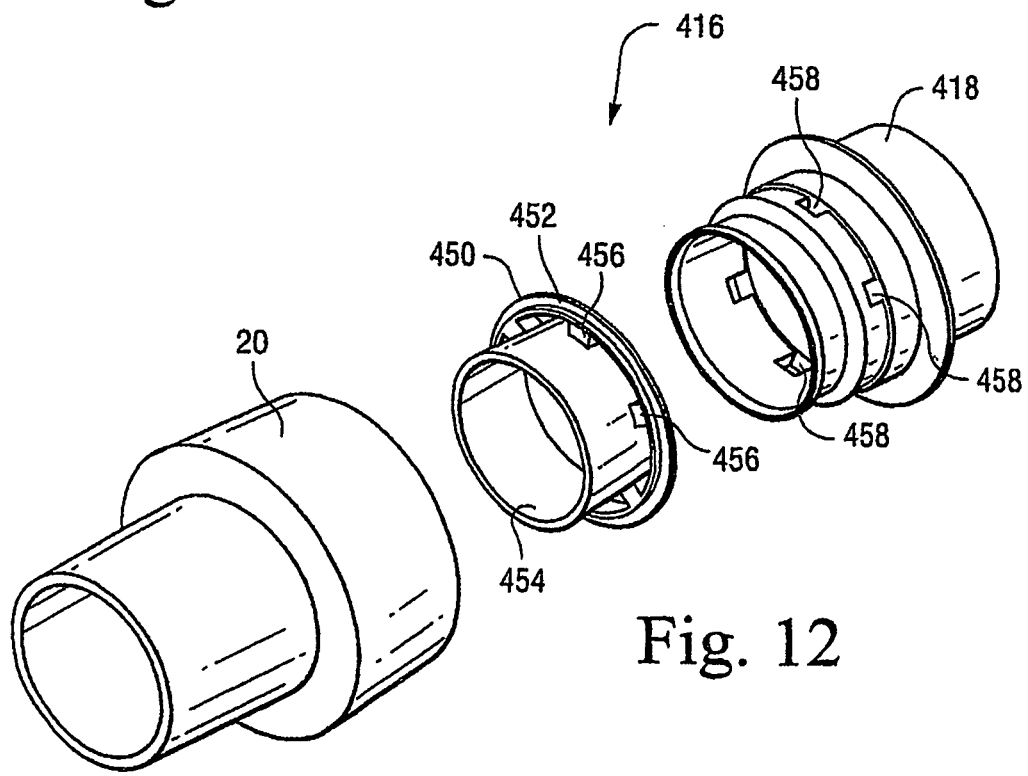
Figure 13:
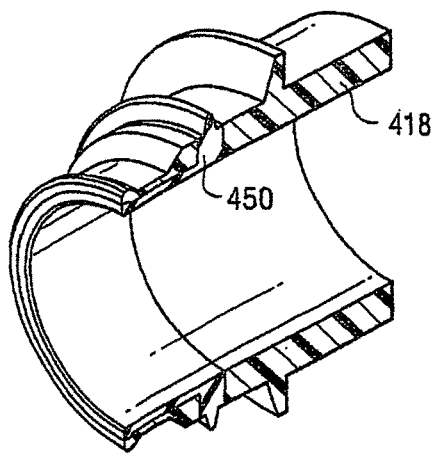
FIGS. 13-15 are cross-sectional views of portion of the swivel elbow shown in FIGS. 11-12 in partial and fully connected states.

FIGS. 9-10 illustrates a swivel elbow 316 constructed according to another exemplary embodiment of the present invention. As illustrated, a lip seal 350 is provided on the elbow 318. In an embodiment, the lip seal 350 is formed of a TPE material and is insert molded to the elbow 318. The lip seal 350 is an internal lip seal in that the lip seal 350 forms a seal with the interior surface 32 of the existing swivel 20. The lip seal 350 improves sealing between the elbow 318 and the swivel 20 without significantly increasing the rotational resistance. Also, the design or material of the swivel 20 does not need to be modified. Further, the internal lip seal 350 is relatively small and positioned between the elbow the swivel so it will not be susceptible to user abuse.

When the swivel 20 is coupled to the elbow 318, the swivel 20 is moved towards the elbow 318 until the protrusion 328 engages with the groove 30 of the swivel 20 with a snap-fit. Moreover, the lip seal 350 engages the interior surface 32 of the swivel 20 and resiliently deforms to form a seal. FIG. 10 shows the assembled position. As illustrated, the leak path between the elbow 318 and the swivel 20 is restricted by the internal lip seal 350. The lip seal 350 contacts the interior surface 32 of the swivel 20 under pressure, but does not substantially increase the rotational resistance.

3.2.1.1 Mechanical Locked Insert Molded TPE (Internal Lip)

The lip seal described above may be provided on the elbow by an insert molding process that includes mechanical locking as well. This allows a large range of material to choose from including existing materials (e.g., POCAN® for the elbow) that do not require chemical bonding. For example, FIGS. 11-15 illustrate an embodiment of swivel elbow 416 having an elbow 418 with a mechanical locked insert molded lip seal 450.

Figure 14:
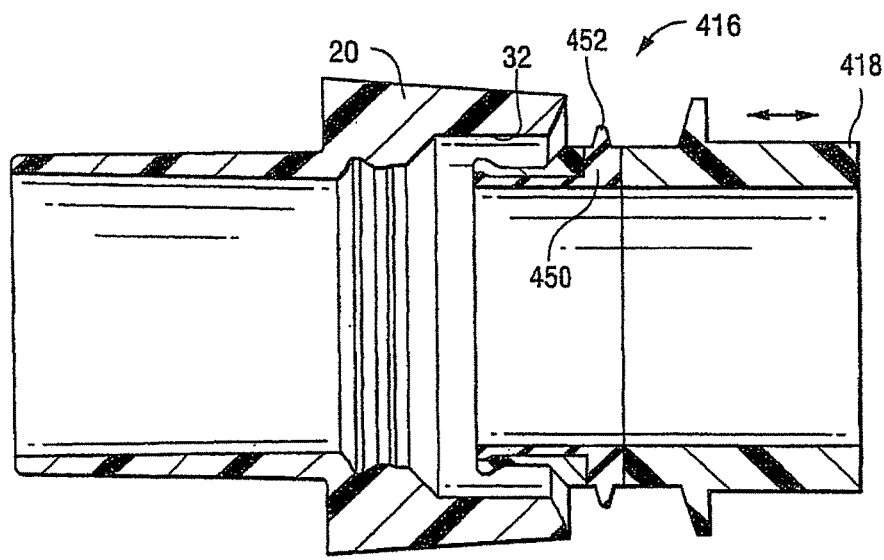
Figure 15:
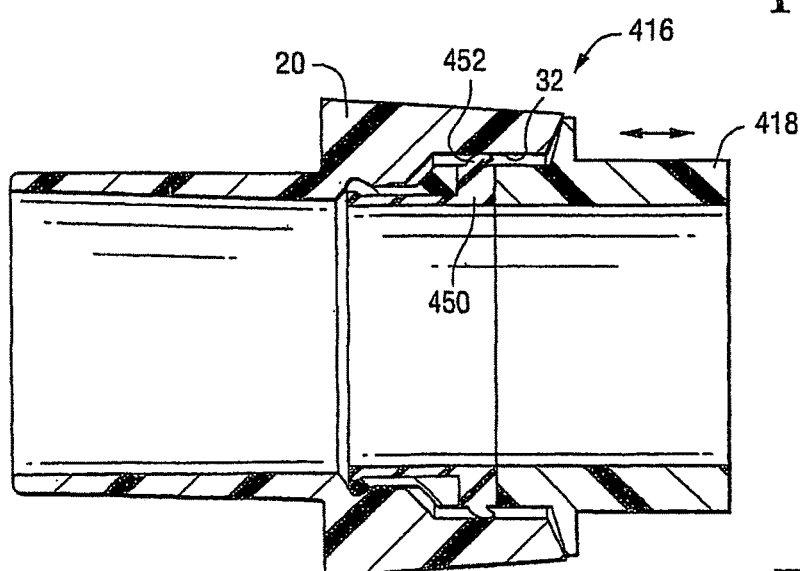

As illustrated, the lip seal 450, e.g., formed of a TPE material or other suitable material, includes a seal portion 452, a tube portion 454, and locking portions 456. When the lip seal 450 is insert molded to the elbow 418, the locking portions 456 interlock with openings 458 provided in the elbow 418. As shown in FIGS. 14-15, the seal portion 452 of the lip seal 450 engages the interior surface 32 of the swivel 20 and resiliently deforms to form a seal.

3.2.2 Insert Molded TPE (External Lip)

Figure 16:
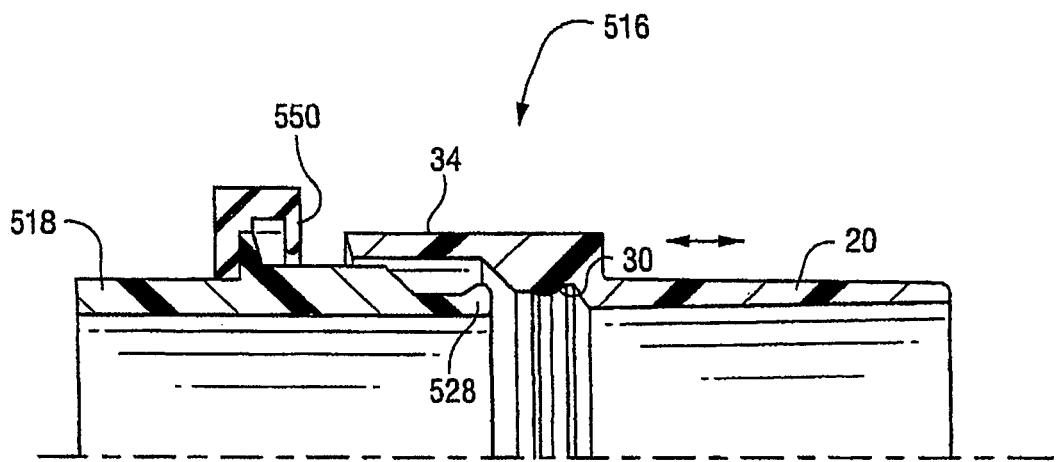
FIGS. 16-17 are cross-sectional views of a portion of a swivel elbow constructed according to another embodiment of the present invention in partial and fully connected states.
Figure 17:
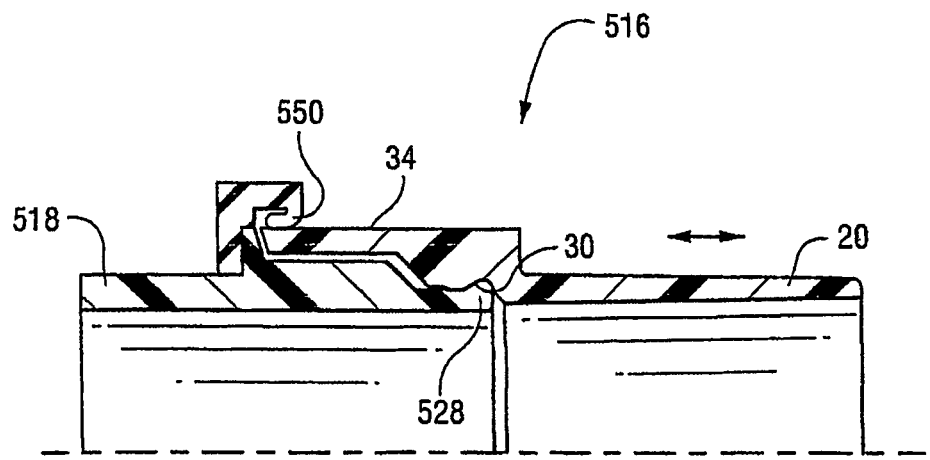

FIGS. 16-17 illustrate a swivel elbow 516 constructed according to another exemplary embodiment of the present invention. As illustrated, a lip seal 550 is provided on the elbow 518. In an embodiment, the lip seal 550 is formed of a TPE material or other suitable material and is insert molded to the elbow 518. The lip seal 550 is an external lip seal in that the lip seal 550 is structured to form a seal with the exterior surface 34 of the existing swivel 20. The lip seal 550 improves sealing between the elbow 518 and the swivel 20 without significantly increasing the rotational resistance. Also, the design or material of the swivel 20 does not need to be modified.

When the swivel 20 is coupled to the elbow 518, the swivel 20 is moved towards the elbow 518 until the protrusion 528 engages with the groove 30 of the swivel 20 with a snap-fit. Moreover, the lip seal 550 engages the exterior surface 34 of the swivel 20 and resiliently deforms to form a seal. FIG. 17 shows the assembled position. As illustrated, the leak path between the elbow 518 and the swivel 20 is restricted by the external lip seal 550. The lip seal 550 contacts the exterior surface 34 of the swivel 20 under pressure, but does not substantially increase the rotational resistance.

The lip seal 550 may be provided on the elbow by an insert molding process that includes mechanical locking as well, similar to the lip seal 450 This allows a large range of material to choose from including existing materials (e.g., POCAN® for the elbow) that do not require chemical bonding. The structure of the elbow 518 may change to include lip locking features, e.g., openings.

3.2.3 Insert Molded TPE (Axial Lip)

Figure 18:
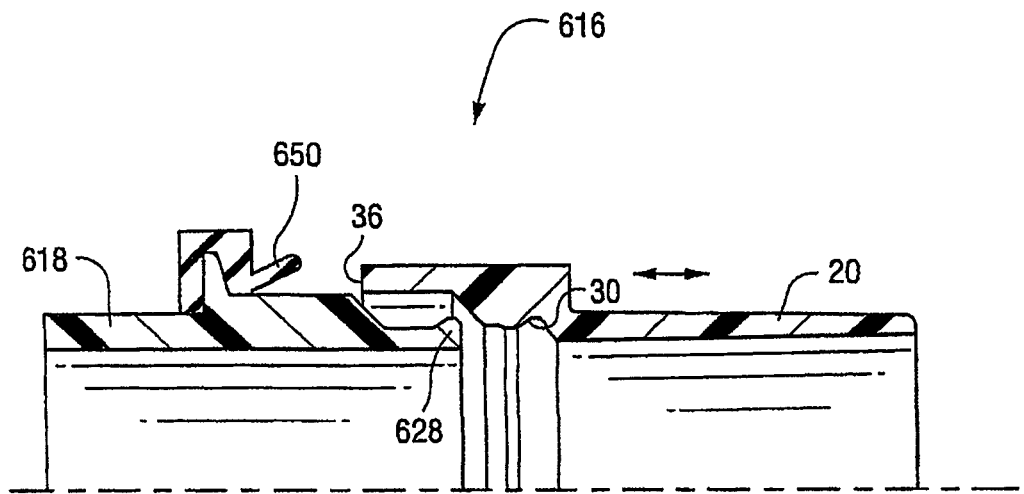
FIGS. 18-19 are cross-sectional views of a portion of a swivel elbow constructed according to another embodiment of the present invention in partial and fully connected states.
Figure 19:
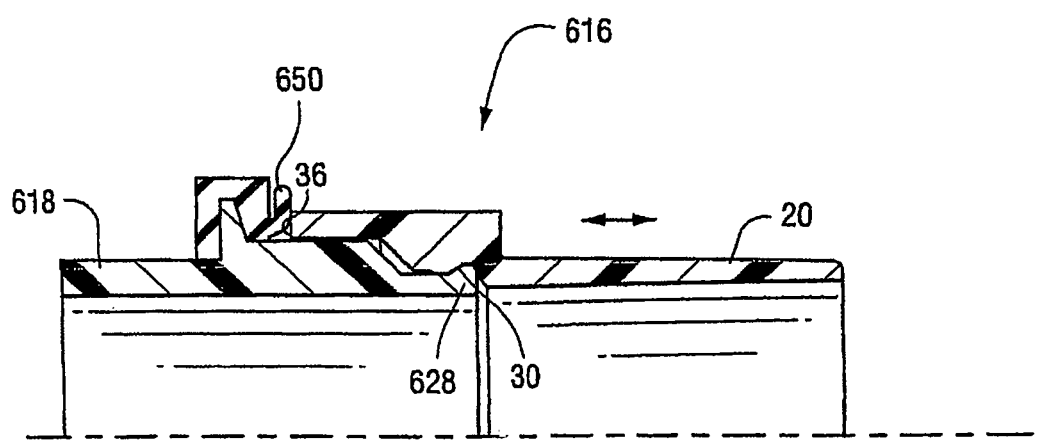

FIGS. 18-19 illustrate a swivel elbow 616 constructed according to another exemplary embodiment of the present invention. As illustrated, a lip seal 650 is provided on the elbow 618. In an embodiment, the lip seal 650 is formed of a TPE material and is insert molded to the elbow 618. The lip seal 650 is an axial lip seal in that the lip seal 650 is structured to form a seal with the front face surface 36 (in the axial direction) of the existing swivel 20. The lip seal 650 improves sealing between the elbow 618 and the swivel 20 without significantly increasing the rotational resistance. Also, the design or material of the swivel 20 does not need to be modified.

When the swivel 20 is coupled to the elbow 618, the swivel 20 is moved towards the elbow 618 until the protrusion 628 engages with the groove 30 of the swivel 20 with a snap-fit. Moreover, the lip seal 650 engages the front face surface 36 of the swivel 20 and resiliently deforms to form a seal. FIG. 19 shows the assembled position. As illustrated, the leak path between the elbow 618 and the swivel 20 is restricted by the external lip seal 650. The lip seal 650 contacts the front face surface 36 of the swivel 20 under pressure, but does not substantially increase the rotational resistance.

The lip seal 650 may be provided on the elbow by an insert molding process that includes mechanical locking as well, similar to the lip seal 450 This allows a large range of material to choose from including existing materials (e.g., POCAN® for the elbow) that do not require chemical bonding. The structure of the elbow 618 may change to include lip locking features, e.g., openings.

3.3 Controlled Interference or Interface Between Swivel/Elbow With Flexible Spring Arm A controlled interference or interface between the swivel and the elbow may also be provided by a flexible spring arm. This flexible spring arm introduces interference to provide a constricted flow path to improve seal. In embodiments, the flexible spring arm may be made with a more flexible material, e.g., polypropylene, instead of existing polycarbonate or POCAN® materials or any other suitable material to reduce the stiffness of the spring arm and introduce inference to improve the sealing feature.

3.3.1 Encapsulated Swivel End

Figure 20:
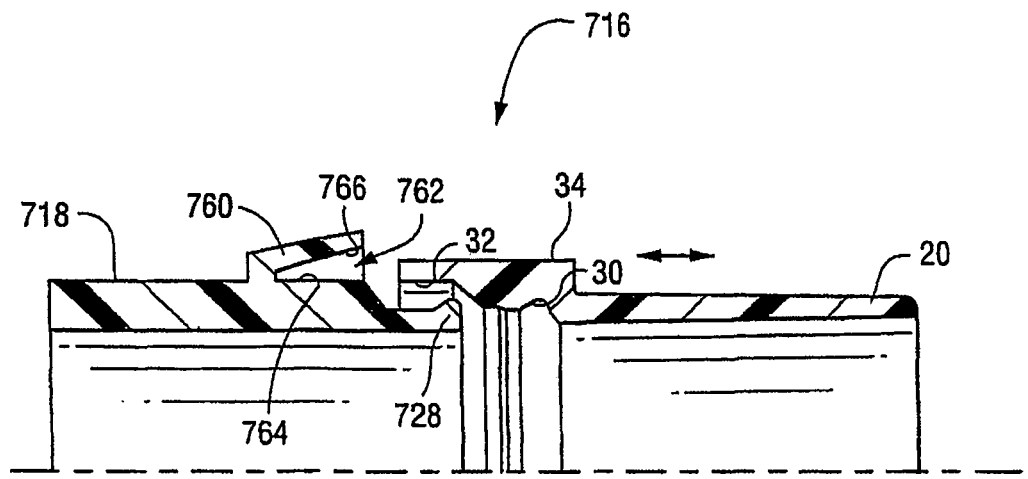
FIGS. 20-21 are cross-sectional views of a portion of a swivel elbow constructed according to another embodiment of the present invention in partial and fully connected states.
Figure 21:
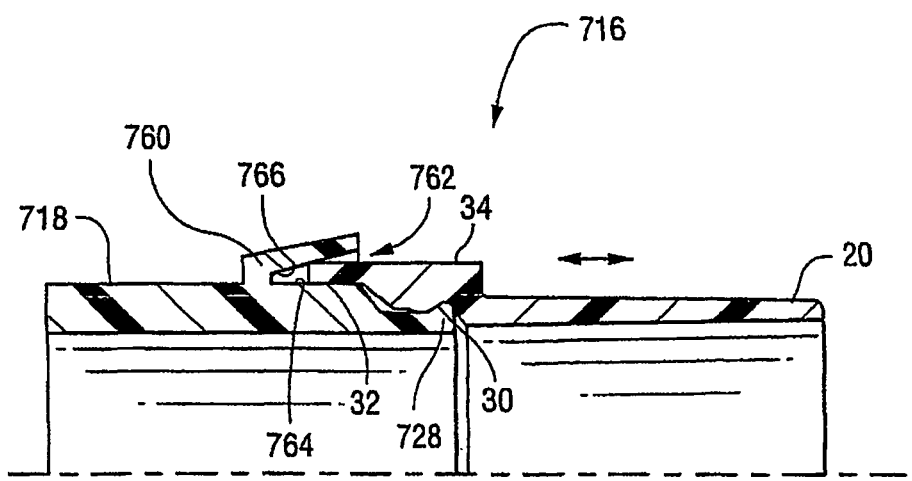

FIGS. 20-21 illustrate a swivel elbow 716 constructed according to another exemplary embodiment of the present invention. As illustrated, a flexible spring arm 760 is provided on the elbow 718. In the illustrated embodiment, the flexible spring arm 760 is formed in one-piece along with the elbow 718. The flexible spring arm 760 allows the elbow 718 to encapsulate the end of the existing swivel 20 so as to form a seal with interior and exterior surfaces 32, 34 of the existing swivel 20. The flexible spring arm 760 improves sealing between the elbow 718 and the swivel 20 without significantly increasing the rotational resistance. Also, the design or material of the swivel 20 does not need to be modified.

As illustrated, the flexible spring arm 760 forms a tapered slot or groove 762 in the elbow 718 to encapsulate the end of the swivel 20. The tapered slot 762 is defined by inner and outer tapered surfaces 764, 766. In an embodiment. the outer tapered surface 766 is steeper than the inner tapered surface 764 and contacts the swivel 20 first during assembly.

When the swivel 20 is coupled to the elbow 718, the swivel 20 is moved towards the elbow 718 until the protrusion 728 engages with the groove 30 of the swivel 20 with a snap-fit. Moreover, the inner and outer tapered surfaces 764, 766 engage interior and exterior surfaces 32, 34 of the swivel 20 to form a seal. The flexible spring arm 760 may flex as the swivel 20 is snap-fit to the elbow 718, which provides an interference fit between the tapered surfaces 764, 766 and the swivel 20. Thus, the elbow 718 encapsulates the end of the swivel 20 and uses interference at two edge contacts to provide two point contact seals. FIG. 21 shows the assembled position: The two seals in series not only improve seal, but also create greater leak resistance to any leaking air.

While there is interference between the elbow 718 and the swivel 20 to create a seal, the contact areas are relatively small. Therefore, the friction torque between the elbow 718 and the swivel 20 is not substantial so as to substantially increase the rotational resistance.

Because the flexible spring arm 760 is formed in one-piece along with the elbow 718, existing materials (e.g., POCAN® for the elbow) may be used. Also, geometric inaccuracies in the elbow 718 (e.g., parallelism and roundness) are accommodated by the tapered surfaces 764, 766 and interference fit.

3.3.2 Encapsulated Swivel End with Spring-Arm Seal

Figure 22:
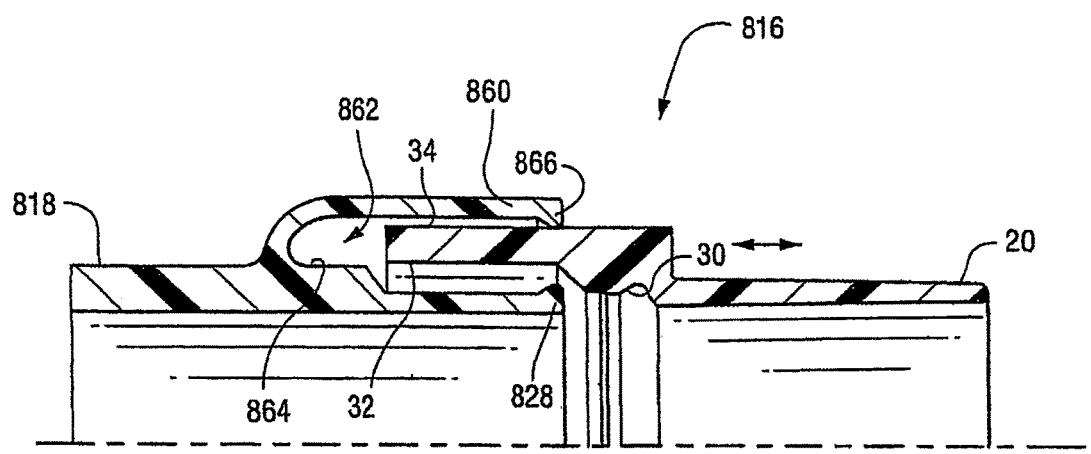
FIGS. 22-23 are cross-sectional views of a portion of a swivel elbow constructed according to another embodiment of the present invention in partial and fully connected states.
Figure 23:
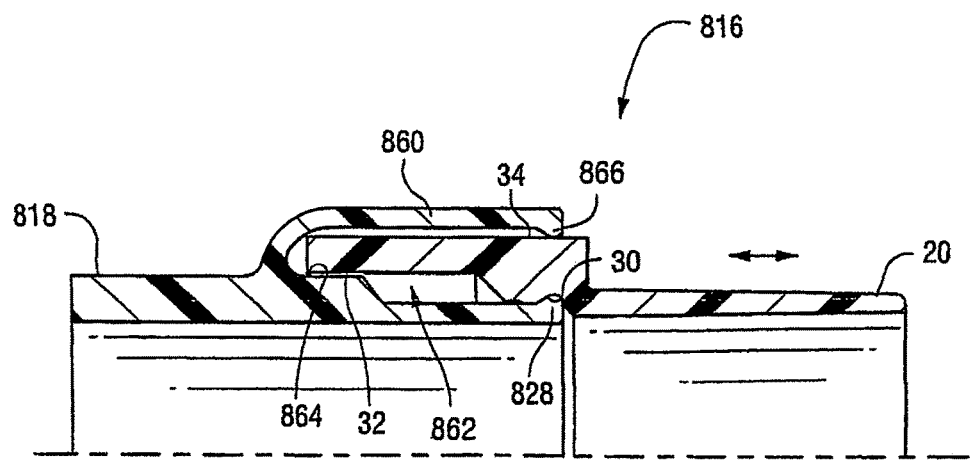

FIGS. 22-23 illustrate a swivel elbow 816 constructed according to another exemplary embodiment of the present invention. As illustrated, a flexible spring arm 860 is provided on the elbow 818. In the illustrated embodiment, the flexible spring arm 860 is formed in one-piece along with the elbow 818. The flexible spring arm 860 allows the elbow 818 to encapsulate the end of the existing swivel 20 and form a seal with the existing swivel 20 at two sealing locations. The flexible spring arm 860 improves sealing between the elbow 818 and the swivel 20 without significantly increasing the rotational resistance. Also, the design or material of the swivel 20 does not need to be modified.

As illustrated, the flexible spring arm 860 is in the form of a thin-walled cylindrical section that forms a slot 862 in the elbow 818 to encapsulate the end of the swivel 20. When the swivel 20 is coupled to the elbow 818, the swivel 20 is moved towards the elbow 818 until the protrusion 828 engages with the groove 30 of the swivel 20 with a snap-fit. Moreover, the inner surface 864 of the slot 862 engages the interior surface 32 of the swivel 20 to form a seal, and the flexible spring arm 860 includes a protrusion 866 that engages the exterior surface 34 of the swivel 20 to form a seal. The flexible spring arm 860 may flex as the swivel 20 is snap-fit to the elbow 818, which provides an interference fit between the protrusion 866 and the swivel 20. Thus, the elbow 818 encapsulates the end of the swivel 20 and provides two contact seals.

The first seal is a controlled clearance annular flow seal between inner surface 864 and interior surface 32. The second seal is a relatively light interference seal between protrusion 866 and exterior surface 34. The designed-in flexibility of the flexible spring arm 860 is intended to allow a relatively stiff material, e.g., such as POCAN®, to provide a relatively small interference force at the outer seal location, which is fairly insensitive to tolerance control. FIG. 23 shows the assembled position. The two seals in series not only improve seal, but also create greater leak resistance to any leaking air.

While there is interference between the elbow 818 and the swivel 20 to create a seal, the contact areas and interference force are relatively small. Therefore, the friction torque between the elbow 818 and the swivel 20 is not substantial so as to substantially increase the rotational resistance.

Because the flexible spring arm 860 is formed in one-piece along with the elbow 818, existing materials (e.g., POCAN® for the elbow) may be used. Also, geometric inaccuracies in the elbow 818 (e.g., parallelism and roundness) are catered for by the flexibility of the spring arm 860.

3.3.3 Lip on Swivel at Sealing Land

FIGS. 24-27 illustrate swivel elbows 916 constructed according to another exemplary embodiment of the present invention. As illustrated, a lip seal 950 is provided on the swivel 920. In the illustrated embodiment, the lip seal 950 is formed in one-piece along with the swivel 920. The lip seal 950 allows the swivel 920 to form a seal with the existing elbow 18 at the sealing land 38 of the elbow 18. The lip seal 950 improves sealing between the elbow 18 and the swivel 920 without significantly increasing the rotational resistance. Also, the design or material of the elbow 18 does not need to be modified.

Figure 24:
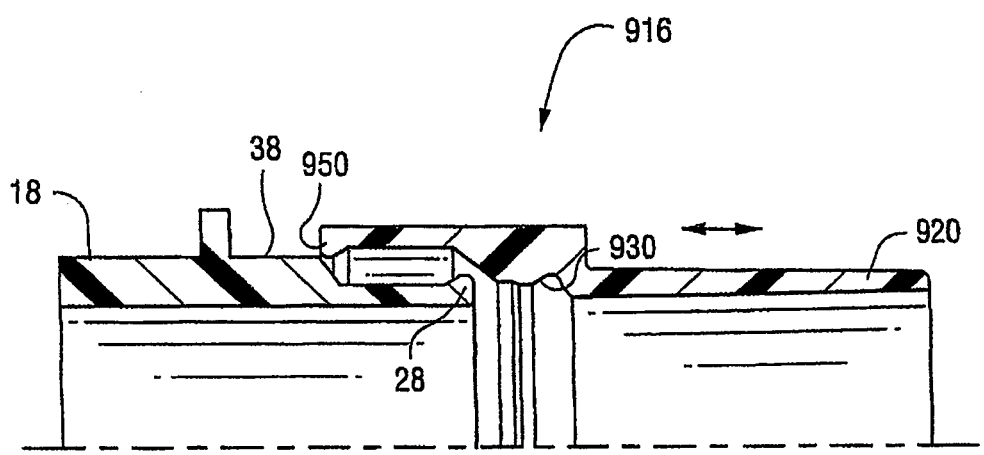
FIGS. 24-25 are cross-sectional views of a portion of a swivel elbow constructed according to another embodiment of the present invention in partial and fully connected states.
Figure 25:
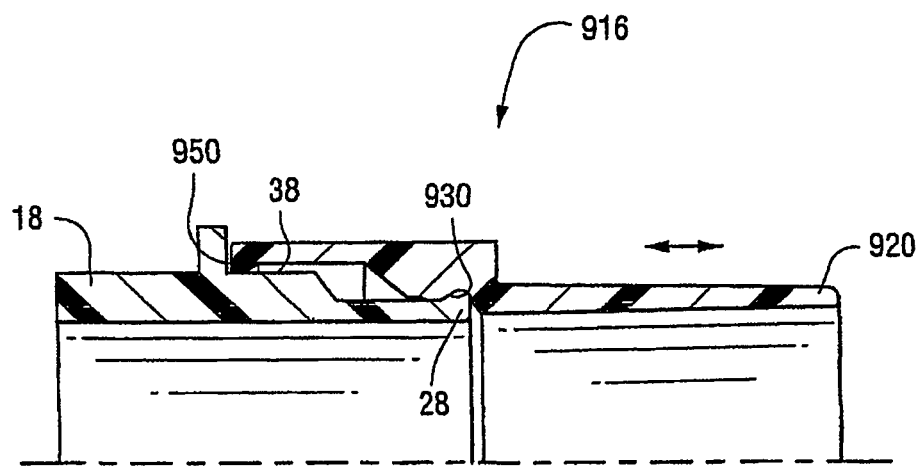
Figure 26:
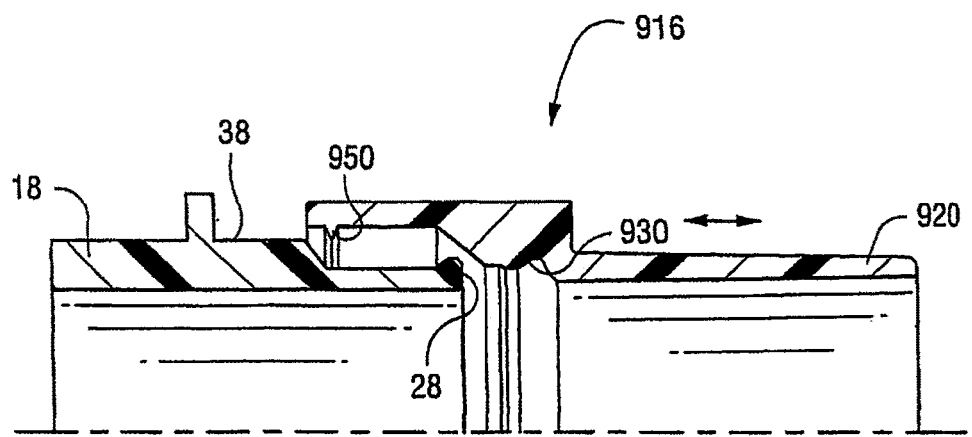
FIGS. 26-27 are cross-sectional views of a portion of a swivel elbow constructed according to another embodiment of the present invention in partial and fully connected states.
Figure 27:
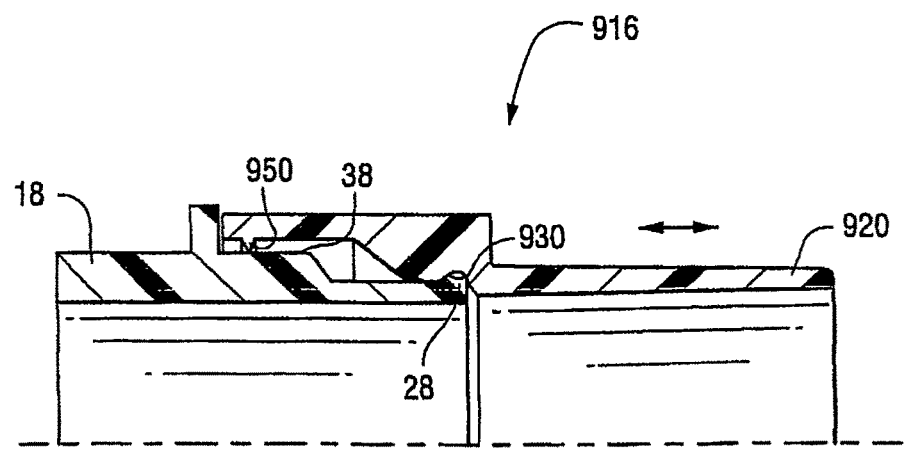
Figure 28:
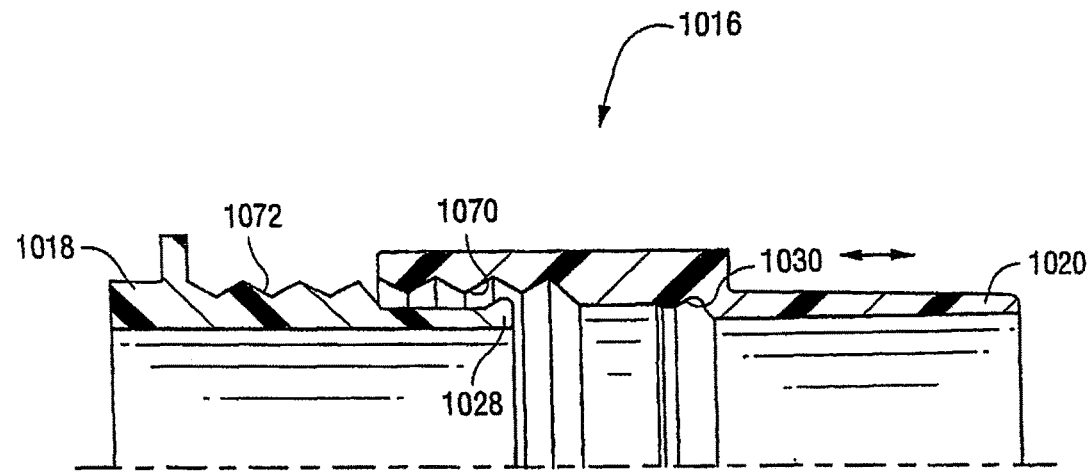
FIGS. 28-29 are cross-sectional views of a portion of a swivel elbow constructed according to another embodiment of the present invention in partial and fully connected states.

As shown in FIGS. 24 and 25, the lip seal 950 may have a rounded configuration. Alternatively, as shown in FIGS. 26 and 27, the lip seal 950 may have a sharper or more pointed configuration. Other configurations are also possible.

When the swivel 920 is coupled to the elbow 18, the swivel 920 is moved towards the elbow 18 until the protrusion 28 engages with the groove 930 of the swivel 920 with a snap-fit. Moreover, the lip seal 950 engages the sealing land 38 of the elbow 18 and resiliently deforms to form a seal. FIGS. 25 and 27 show the assembled positions of both lip seal configurations. As illustrated, the leak path between the elbow 18 and the swivel 920 is restricted by the lip seal 950. The lip seal 950 contacts the sealing land 38 of the elbow 18 under pressure, but does not substantially increase the rotational resistance.

Both sealing lip configurations use a lip seal 950 to create interference between the swivel 920 and the sealing land 38 of the elbow 18. The main difference between the two configurations is in the amount of contact pressure generated between the lip seal 950 and the sealing land 38. For example, because the sharper lip seal 950 has a smaller contact area with the elbow 18, it creates greater contact pressure and hence more interference and presumably better seal. In an embodiment, the sharper lip seal 950 of the swivel 920 may create a very small groove in the sealing land 38 of the elbow 18 which may help to even out the effects of poor roundness and further improve the seal.

While there is interference between the elbow 18 and the swivel 920 to create a seal, the contact areas and interference force are relatively small. Therefore, the friction torque between the elbow 18 and the swivel 920 is not substantial so as to substantially increase the rotational resistance.

Because the lip seal 950 is formed in one-piece along with the swivel 920, existing materials (e.g., polycarbonate for the swivel) may be used. Also, geometric inaccuracies in the elbow 18 (e.g., parallelism and roundness) are catered for by the interference fit.

3.4 Long Sealing Path Between Swivel/Elbow To Provide a Constricted Flow Path

A long sealing path or more tortuous sealing path may be provided between the elbow and the swivel to control the inadvertent leak between these parts.

3.4.1 Long Sealing Path—External Seal Only

FIGS. 28-31 illustrate swivel elbows 1016 constructed according to another exemplary embodiment of the present invention. As illustrated, a saw-tooth shaped sealing land 1070 is provided on the swivel 1020 and a saw-tooth shaped sealing land 1072 is provided on the elbow 1018. In the illustrated embodiment, the sealing land 1070 is formed in one-piece along with the swivel 1020 and the sealing land 1072 is formed in one-piece along with the elbow 1018. The saw-tooth shaped sealing lands 1070, 1072 compensate for poor geometric accuracy in the elbow 1018 by introducing a tortuous flow path for the leaking air. The saw-tooth shaped sealing lands 1070, 1072 improve sealing between the swivel 1020 and the elbow 1018 without significantly increasing the rotational resistance.

Figure 30:
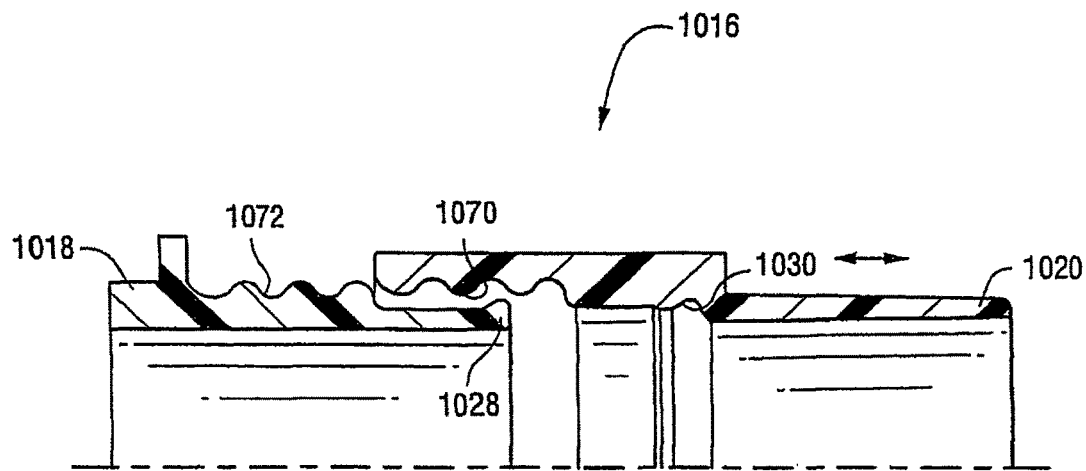
FIGS. 30-31 are cross-sectional views of a portion of a swivel elbow constructed according to another embodiment of the present invention in partial and fully connected states.
Figure 31:
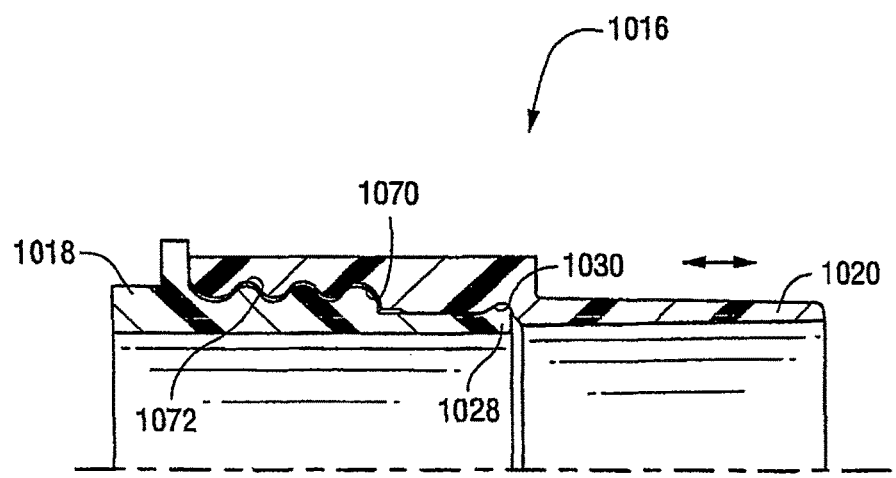

In the illustrated embodiment, the sealing lands 1070, 1072 have complementary saw-tooth configurations. As illustrated, each sealing land 1070, 1072 has about 3 saw teeth. However, any suitable number of saw teeth may be provided, e.g., 1, 2, or 3 saw teeth. Alternatively, the sealing lands 1070, 1072 may have complementary wave-like configurations as shown in FIGS. 30-31. Other configurations are also possible.

Figure 29:
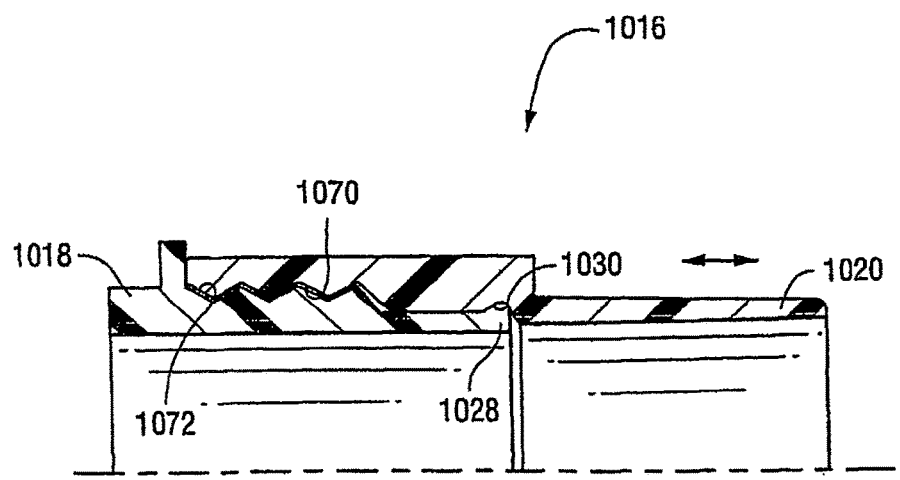

When the swivel 1020 is coupled to the elbow 1018, the swivel 1020 is moved towards the elbow 1018 until the protrusion 1028 engages with the groove 1030 of the swivel 1020 with a snap-fit. Moreover, the sealing lands 1070, 1072 engage with One another in a complimentary relation to form a seal. The design of the saw-tooth or wave profile generates a relatively light detent feel as the parts pass over each other during assembly & disassembly. FIGS. 29 and 31 show the assembled positions of both configurations. As illustrated, the leak path between the elbow 1018 and the swivel 1020 is saw-like, wave-like, or tortuous.

As pressure is introduced to the mask, the elbow 1018 and swivel 1020 may tend to separate axially from each other until restrained by contact between the saw-tooth shaped sealing lands 1070, 1072. This contact will further aid the seal that is generated by the tortuous flow path.

Because the saw-tooth or wave shaped sealing lands 1070, 1072 are formed in one-piece along with the swivel 1020 and the elbow 1018, existing materials (e.g., POCAN® for the elbow and polycarbonate for the swivel) may be used or some other suitable material. Also, the interference between the elbow 1018 and the swivel 1020 is not substantial so as to substantially increase the rotational resistance.

3.4.2 Inner and Outer Seal with Existing Elbow

FIGS. 32-35 illustrate swivel elbows 1116 constructed according to another exemplary embodiment of the present invention. As illustrated, a flexible spring arm 1160 is provided on the swivel 1120. In the illustrated embodiment, the flexible spring arm 1160 is formed in one-piece along with the swivel 1160. The flexible spring arm 1160 allows the swivel 1120 to encapsulate the end of the existing elbow 18 and form a seal with the existing elbow 18 at two sealing locations. The flexible spring arm 1160 improves sealing between the elbow 18 and the swivel 1120 without significantly increasing the rotational resistance. Also, the design or material of the elbow 18 does not need to be modified.

Figure 32:
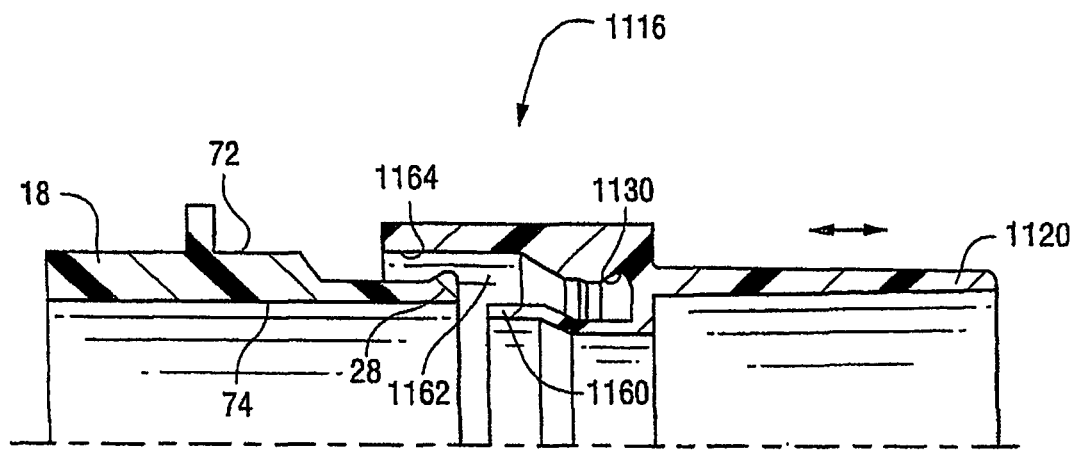
FIGS. 32-33 are cross-sectional views of a portion of a swivel elbow constructed according to another embodiment of the present invention in partial and fully connected states.
Figure 33:
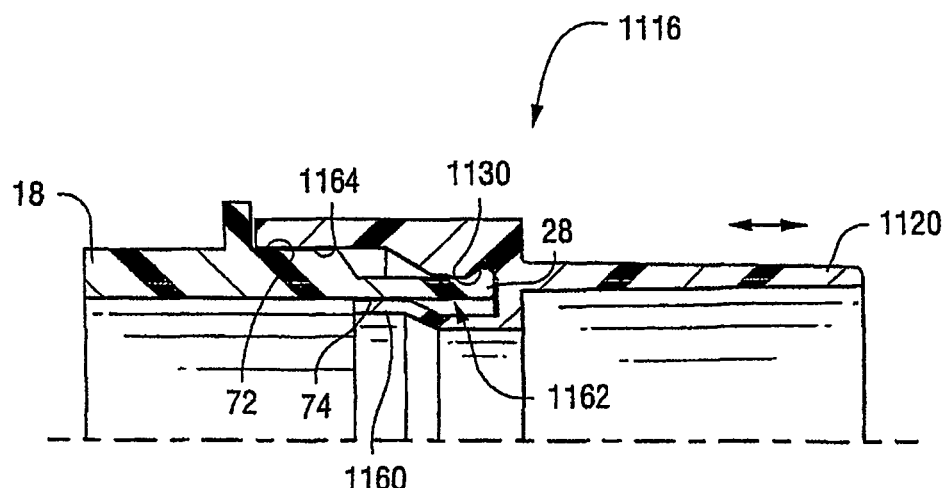
Figure 34:
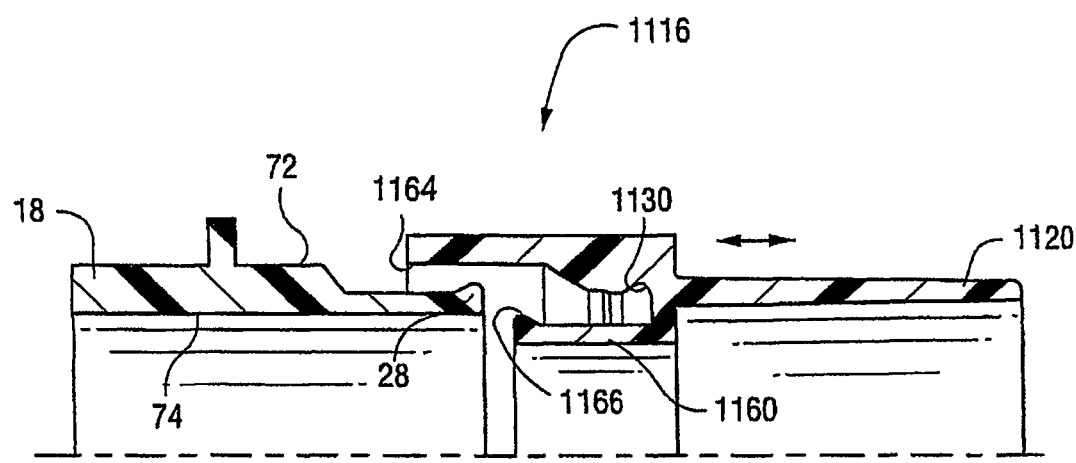
FIGS. 34-35 are cross-sectional views of a portion of a swivel elbow constructed according to another embodiment of the present invention in partial and fully connected states.
Figure 35:
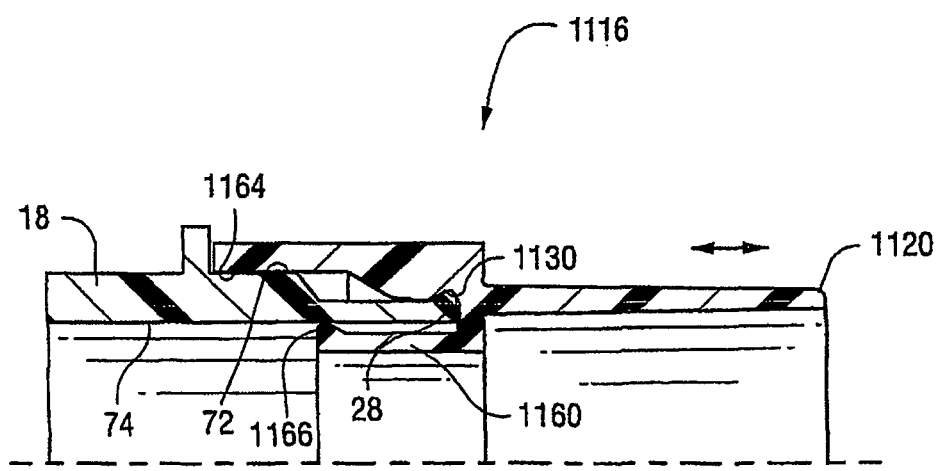

As shown in FIGS. 32 and 33, the flexible spring arm 1160 may have a planar or flat sealing surface. Alternatively, as shown in FIGS. 34 and 35, the flexible spring arm 1160 may have a protrusion or lip 1166 that provides a sealing surface. Other configurations are also possible.

The flexible spring arm 1160 forms a slot 1162 in the swivel 1120 to encapsulate the end of the elbow 18. When the swivel 1120 is coupled to the elbow 18, the swivel 1120 is moved towards the elbow 18 until the protrusion 28 engages with the groove 1130 of the swivel 1120 with a snap-fit. Moreover, the inner surface 1164 of the swivel 1120 engages the exterior sealing land 72 of the elbow 18 to form a seal, and the flexible spring arm 1160 engages the interior surface 74 of the elbow 18 to form a seal. Thus, the swivel 1120 encapsulates the end of the elbow 18 and provides two contact seals. FIGS. 33 and 35 show the assembled positions of both spring arm configurations. The two seals in series net only improve seal, but also create greater leak resistance to any leaking air.

While there is interference between the elbow 18 and the swivel 1120 to create a seal, the contact areas and interference force are relatively small. Therefore, the friction torque between the elbow 18 and the swivel 1120 is not substantial so as to substantially increase the rotational resistance.

Because the flexible spring arm 1160 is formed in one-piece along with the swivel 1120, existing materials (e.g., polycarbonate for the swivel) may be used. Also, the swivel design shown in FIGS. 34-35 may provide easier removal of the swivel from a mold core.

3.4.3 Inner and Outer Seal—Relocated Snap

Figure 36:
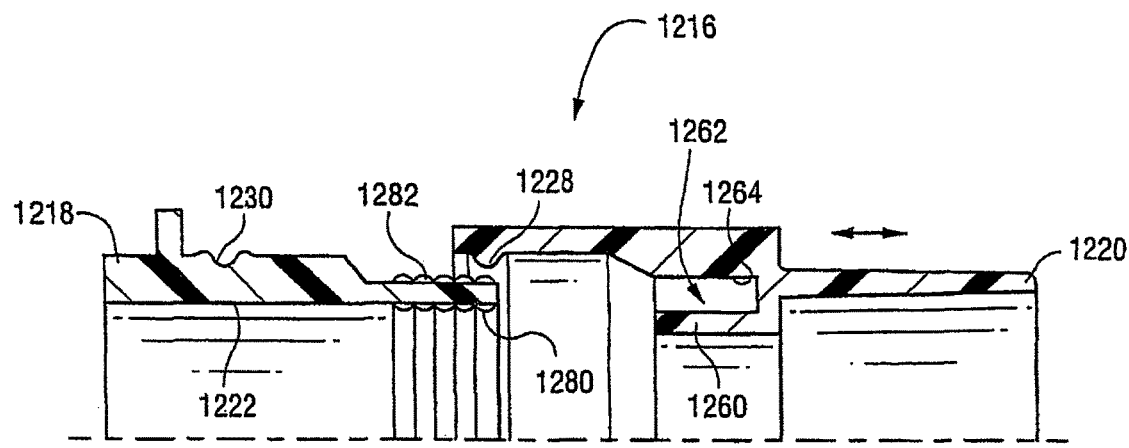
FIGS. 36-37 are cross-sectional views of a portion of a swivel elbow constructed according to still another embodiment of the present invention in partial and fully connected states.
Figure 37:
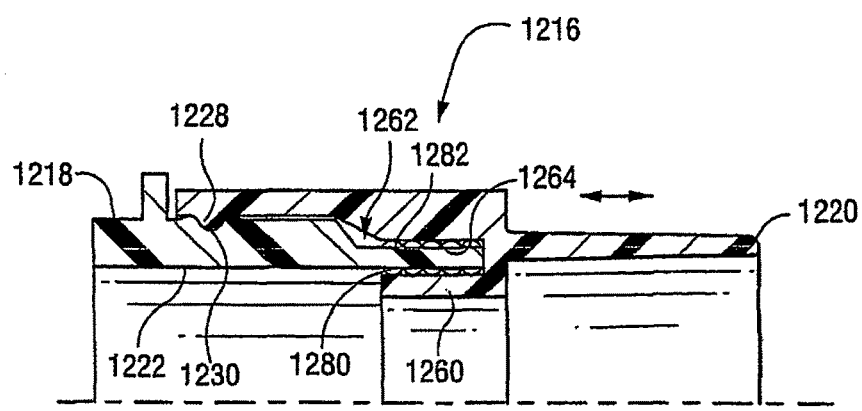
Figure 38:
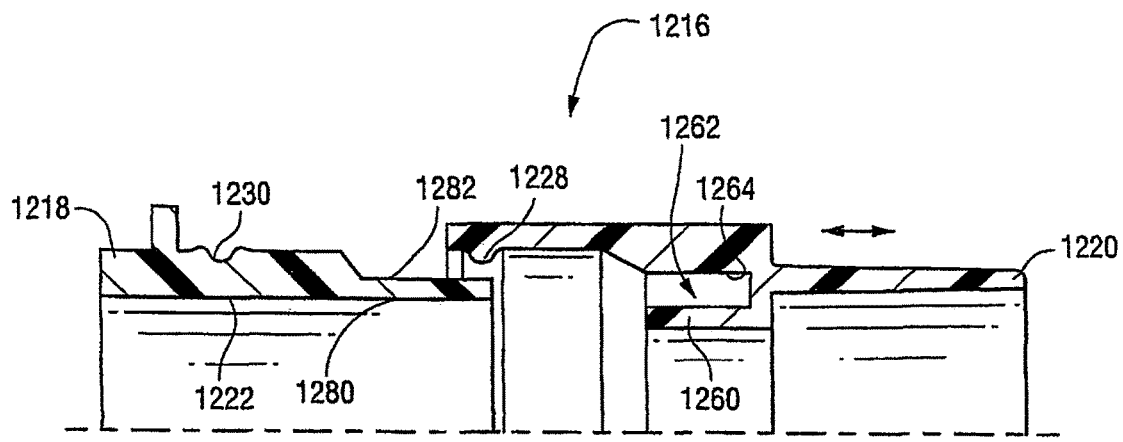
FIGS. 38-39 are cross-sectional views of a portion of a swivel elbow constructed according to yet another embodiment of the present invention in partial and fully connected states.
Figure 39:
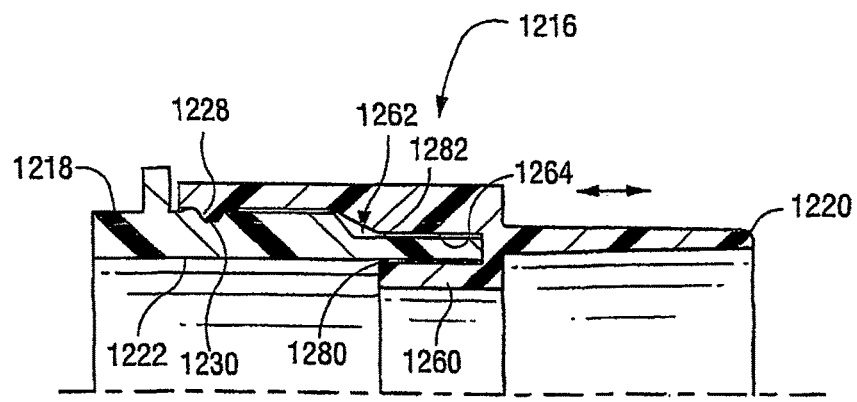

FIGS. 36-39 illustrate swivel elbows 1216 constructed according to yet another exemplary embodiment of the present invention. As illustrated, the location of the snap-fit and sealing have been swapped with respect to swivel elbows described above, e.g., FIGS. 32-35. Specifically, a flexible spring arm 1260 is provided on a non-patient end of the swivel 1220, and a protrusion 1228 is provided on a patient end of the swivel 1220. Also, a groove 1230 is provided on a inner portion of the inlet conduit 1222 of the elbow 1218, and inner and outer sealing protrusions 1280, 1282 are provided on inner and outer surfaces of the outer portion of the inlet conduit 1222. Alternatively, the inner and outer surfaces of the outer portion of the inlet conduit 1222 may have substantially flat sealing lands 1280, 1282 for a controlled clearance seal as shown in FIGS. 38-39. Other configurations are also possible.

In the illustrated embodiment, the flexible spring arm 1260 is formed in one-piece along with the swivel 1220, and the sealing lands 1280, 1282 are formed in one-piece along with the elbow 1218. The flexible spring arm 1260 allows the swivel 1220 to encapsulate the end of the elbow 1218 and form a seal with the elbow 1218 at two sealing locations. The flexible spring arm 1260 improves sealing between the elbow 1218 and the swivel 1220 without significantly increasing the rotational resistance.

The flexible spring arm 1260 forms a slot 1262 in the swivel 1220 to encapsulate the end of the elbow 1218. When the swivel 1220 is coupled to the elbow 1218, the swivel 1220 is moved towards the elbow 1218 until the protrusion 1228 engages with the groove 1230 of the elbow 1218 with a snap-fit. Moreover, the inner surface 1264 of the swivel 1220 engages the outer sealing lands 1282 of the elbow 1218 to form a seal, and the flexible spring arm 1260 engages the inner sealing lands 1280 of the elbow 1218 to form a seal. Thus, the swivel 1220 encapsulates the end of the elbow 1218 and provides two contact seals. FIGS. 37 and 39 show the assembled positions of both configurations. The two seals in series not only improve seal, but also create greater leak resistance to any leaking air. As illustrated in FIGS. 36-37, the leak path between the elbow 1218 and the swivel 1220 is wave-like or tortuous.

While there is interference between the elbow 1218 and the swivel 1220 to create a seal, the contact areas and interference force are relatively small. Therefore, the friction torque between the elbow 1218 and the swivel 1220 is not substantial so as to substantially increase the rotational resistance.

Because the flexible spring arm 1260 is formed in one-piece along with the swivel 1220 and the sealing lands 1280, 1282 are formed in one-piece along with the elbow 1218, existing materials (e.g., POCAN® for the elbow and polycarbonate for the swivel) may be used. Also, the swivel design may provide easier removal of the swivel from a mold core.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A swivel elbow for a mask assembly to supply pressurized breathable gas, comprising:
    an elbow adapted to be provided to the mask assembly; and
    a swivel detachably connected to the elbow,
    wherein the elbow includes a plurality of spaced apart rings that provide a controlled clearance between the elbow and an interior surface of the swivel, the controlled clearance being configured to control a leak rate of the pressurized breathable gas from the mask assembly and between the elbow and the swivel,
    wherein the leak rate is a non-zero leak rate.

2. The swivel elbow according to claim 1, wherein one of the elbow and the swivel includes a radially extending protrusion that locks in place within a groove provided in the other of the elbow and the swivel with a snap-fit.

3. The swivel elbow according to claim 1, wherein the elbow includes three spaced apart rings.

4. A mask assembly for a patient, comprising: a frame; a cushion provided to the frame; and a swivel elbow according to claim 1 provided to the frame.

5. The swivel elbow according to claim 1, wherein the controlled clearance is about 0.05-0.3 mm between the elbow and the swivel.

6. The swivel elbow according to claim 1, wherein each of the rings includes a width of about 1 mm.

7. The swivel elbow according to claim 1, wherein the rings are spaced apart from one another by about 1.2 mm.

8. The swivel elbow according to claim 1, wherein the elbow includes greater than three of the spaced apart rings.

9. The swivel elbow according to claim 1, wherein the elbow includes less than three of the spaced apart rings.

10. The swivel elbow according to claim 1, wherein the controlled clearance controls leak without significantly increasing rotational resistance.

11. The swivel elbow according to claim 1, wherein the controlled clearance reduces leak rate and controls variation in leak rate between the elbow and the swivel.

12. The swivel elbow according to claim 1, wherein the rings maintain uniform wall sections throughout the elbow.

13. The swivel elbow according to claim 1, wherein the elbow includes an inlet conduit, and the plurality of spaced apart rings are provided to the inlet conduit.

14. The swivel elbow according to claim 13, further comprising a collar provided to the inlet conduit, the collar positioned downstream from the plurality of spaced apart rings.

15. The swivel elbow according to claim 14, wherein the swivel includes a front face surface that engages the collar.

16. The swivel elbow according to claim 13, wherein the inlet conduit does not include a collar provided thereto.

17. The swivel elbow according to claim 13, wherein the inlet conduit comprises a plurality of resiliently deformable tabs having protrusions to detachably connect the inlet conduit to the swivel.

18. The swivel elbow according to claim 17, wherein each of the plurality of resiliently deformable tabs are separated by notches disposed around an end of the inlet conduit.

19. The swivel elbow according to claim 1, wherein the pressurized breathable gas leaks from the mask assembly at an overall leak rate and the leak rate through the swivel elbow forms part of the overall leak rate.

* * * * *